(12) United States Patent
Slautterback

(10) Patent No.: US 6,419,652 B1
(45) Date of Patent: Jul. 16, 2002

(54) BACK BELT AND METHOD

(75) Inventor: E. G. Slautterback, Coral Springs, FL (US)

(73) Assignee: FLA Orthopedics, Inc., Miramar, FL (US)

( * ) Notice: Subject to any disclaimer, the term of this patent is extended or adjusted under 35 U.S.C. 154(b) by 0 days.

(21) Appl. No.: 09/420,882

(22) Filed: Oct. 19, 1999

(51) Int. Cl.[7] .................. A61F 5/00; A61F 5/28; A41F 9/00
(52) U.S. Cl. .................. 602/19; 128/96.1; 2/311
(58) Field of Search .............. 602/5, 19, 60–62; 128/845–846, 869, 875, 96.1, 99.1, 100.1–101.1, 106.1; 2/44, 311, 338; 482/106

(56) References Cited

U.S. PATENT DOCUMENTS

| | | | |
|---|---|---|---|
| 3,717,143 A | * 2/1973 | Johnson | 128/78 |
| 4,513,449 A | * 4/1985 | Donzis | 2/2 |
| 4,833,730 A | * 5/1989 | Nelson | 2/44 |
| 5,147,261 A | 9/1992 | Smith et al. | 482/106 |
| 5,188,585 A | * 2/1993 | Peters | 602/19 |
| 5,207,635 A | * 5/1993 | Richards et al. | 602/19 |
| 5,388,274 A | * 2/1995 | Glover et al. | 2/338 |
| 5,437,614 A | * 8/1995 | Grim | 602/19 |
| 5,656,021 A | 8/1997 | Greengarg | 602/19 |
| 5,722,940 A | * 3/1998 | Gaylord, Jr. et al. | 602/19 |

* cited by examiner

Primary Examiner—Denise M. Pothier

(57) ABSTRACT

A formable plastic polyolefin material being sold by the Trademark VOLARA® relates to the back support product of the invention. The formable material, with the fabric laminated preferably to both surfaces, is either cut to shape by standard clickers, heat cutting, or other means and then inserted into a die mold where it is formed by compression and heat. The compression and heat are primarily directed to forming channels for stays to be later inserted, and also to form the lateral edge tongues and pockets for securement of the inner wrap ends. The VOLARA® material is desirably laminated on both sides with the external laminate being a nylon, a mesh, sewable fabric. On the other hand, the inside laminate is a coated non-slip copolymer material. Once the compression pad is formed to shape, the stays are placed in position in the stay channels and webbing applied over the stays and stitched to form a pocket for the stays along with the channel, and thereby secure the integrity of the back portion of the belt. The outer peripheral portion of the entire unit has a ribbing applied and the same, by way of binding effect, assists in securing the components together.

1 Claim, 6 Drawing Sheets

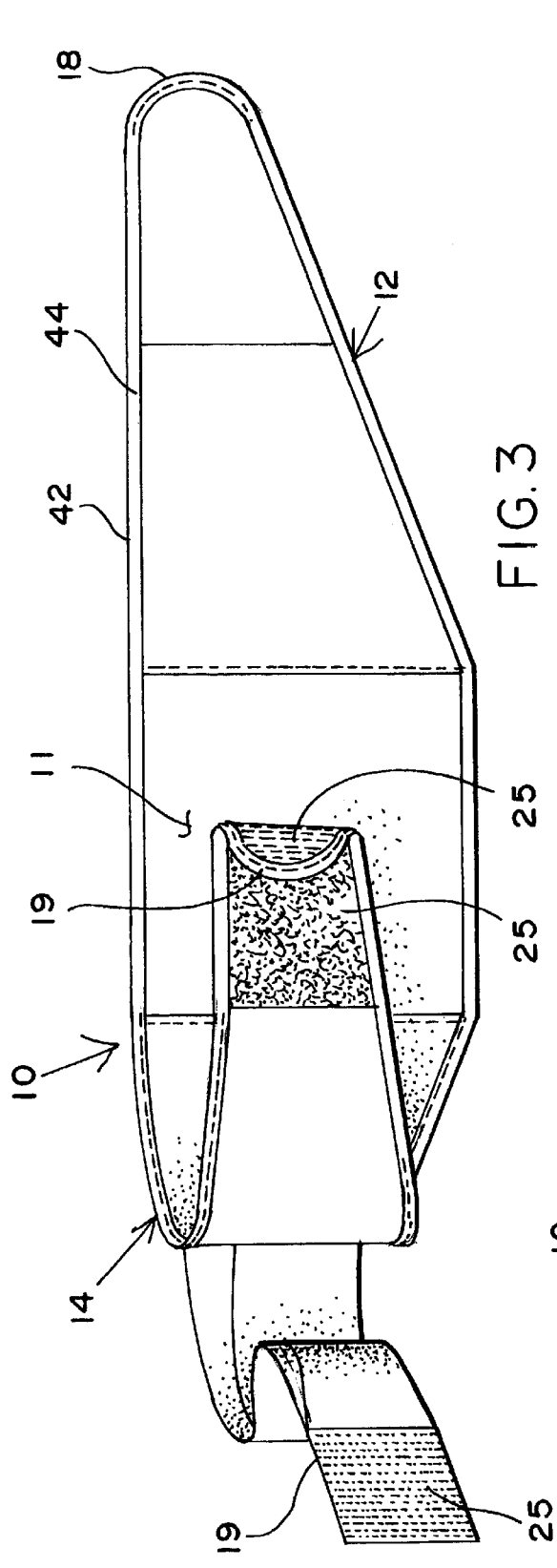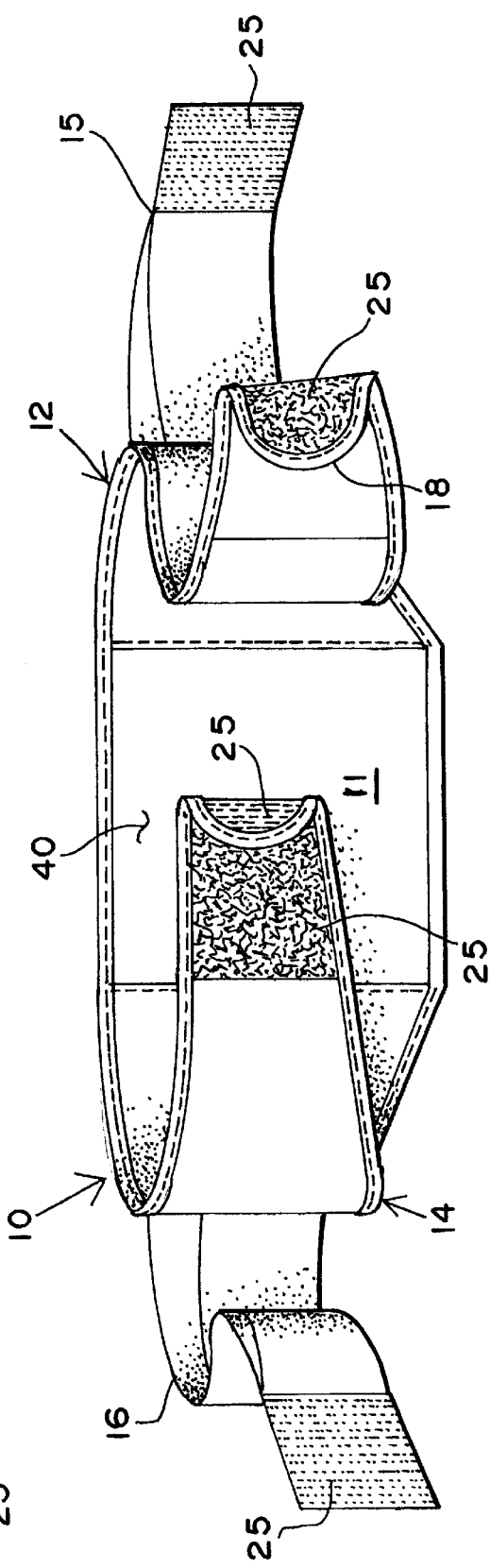

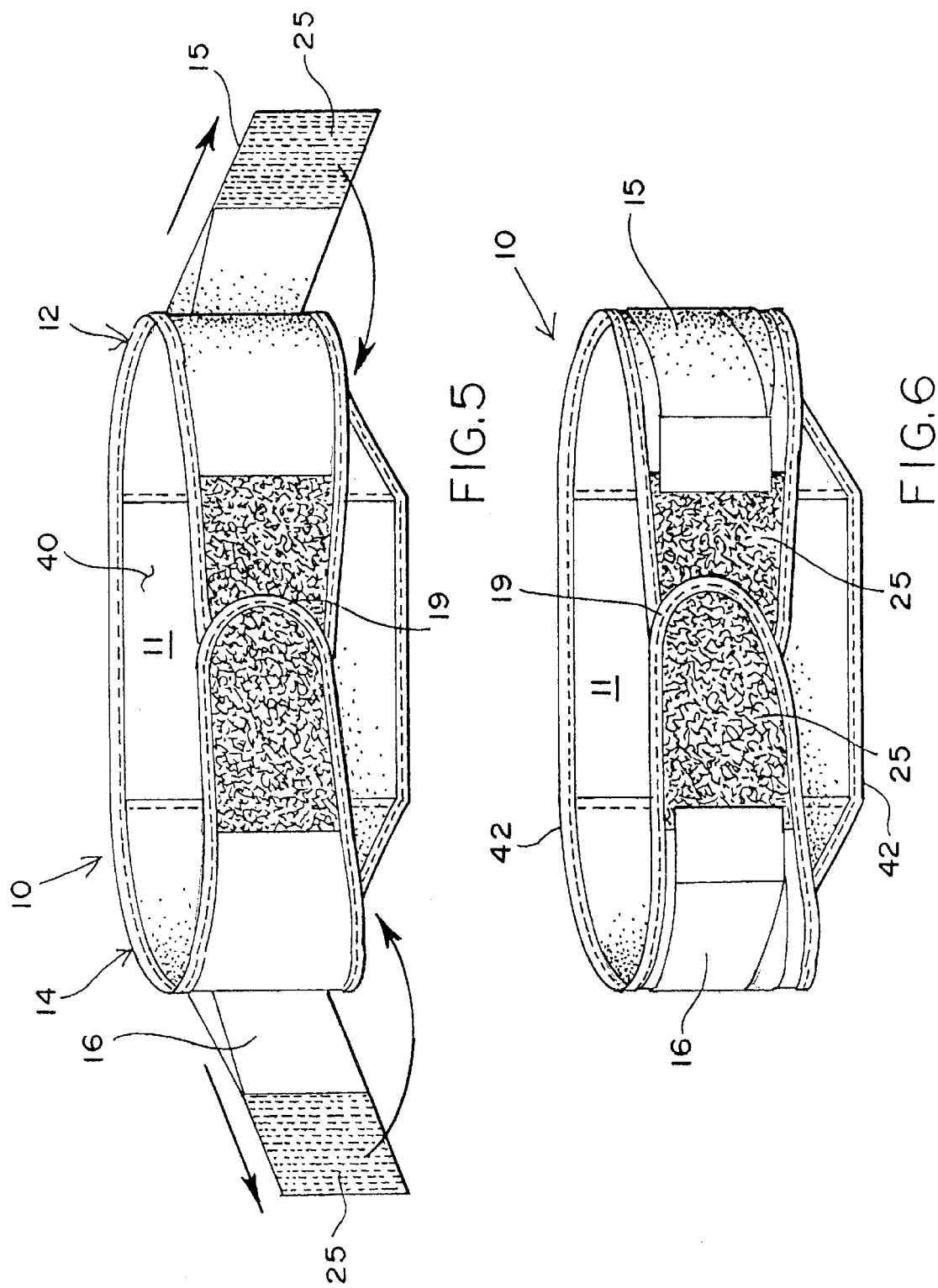

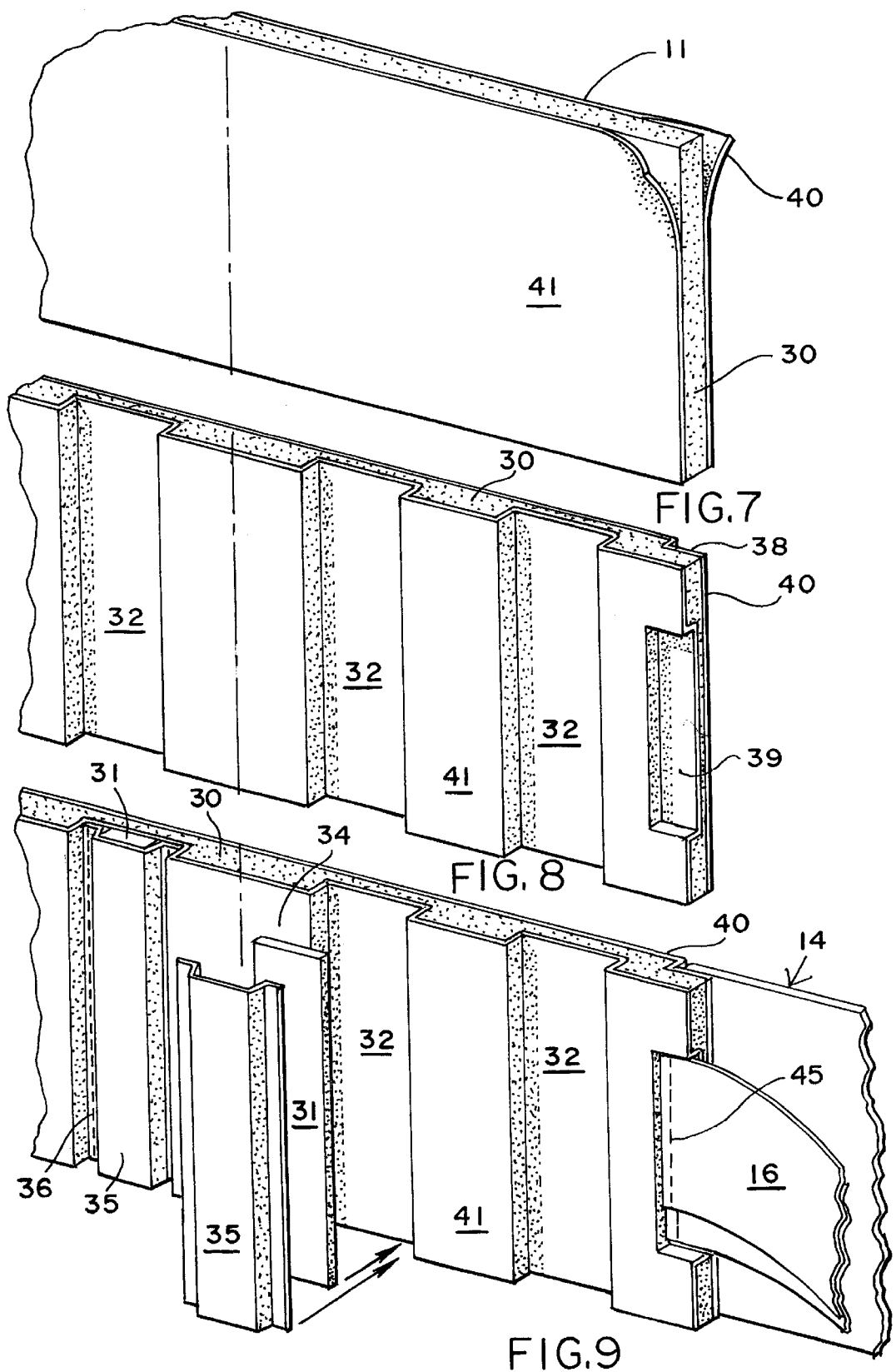

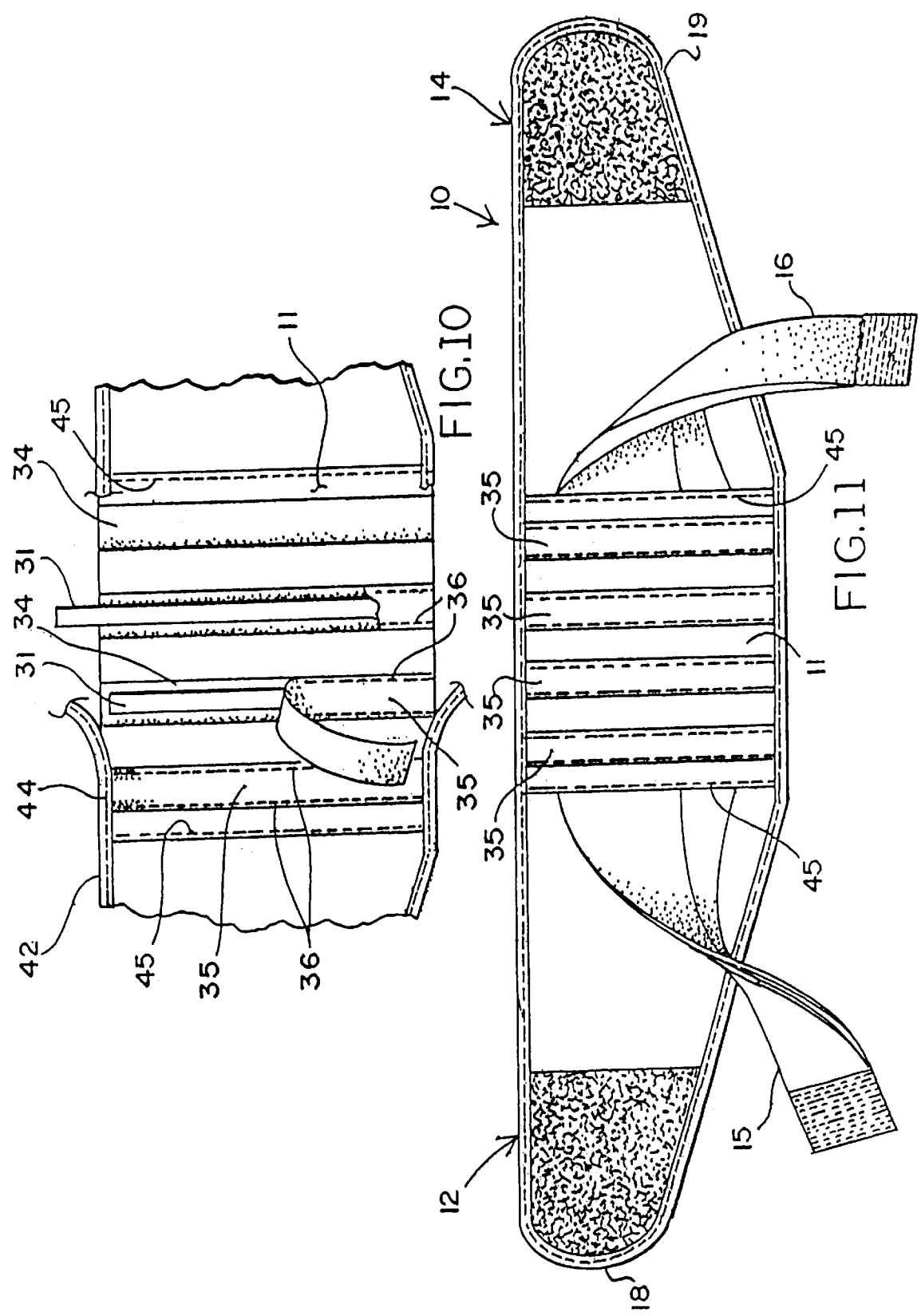

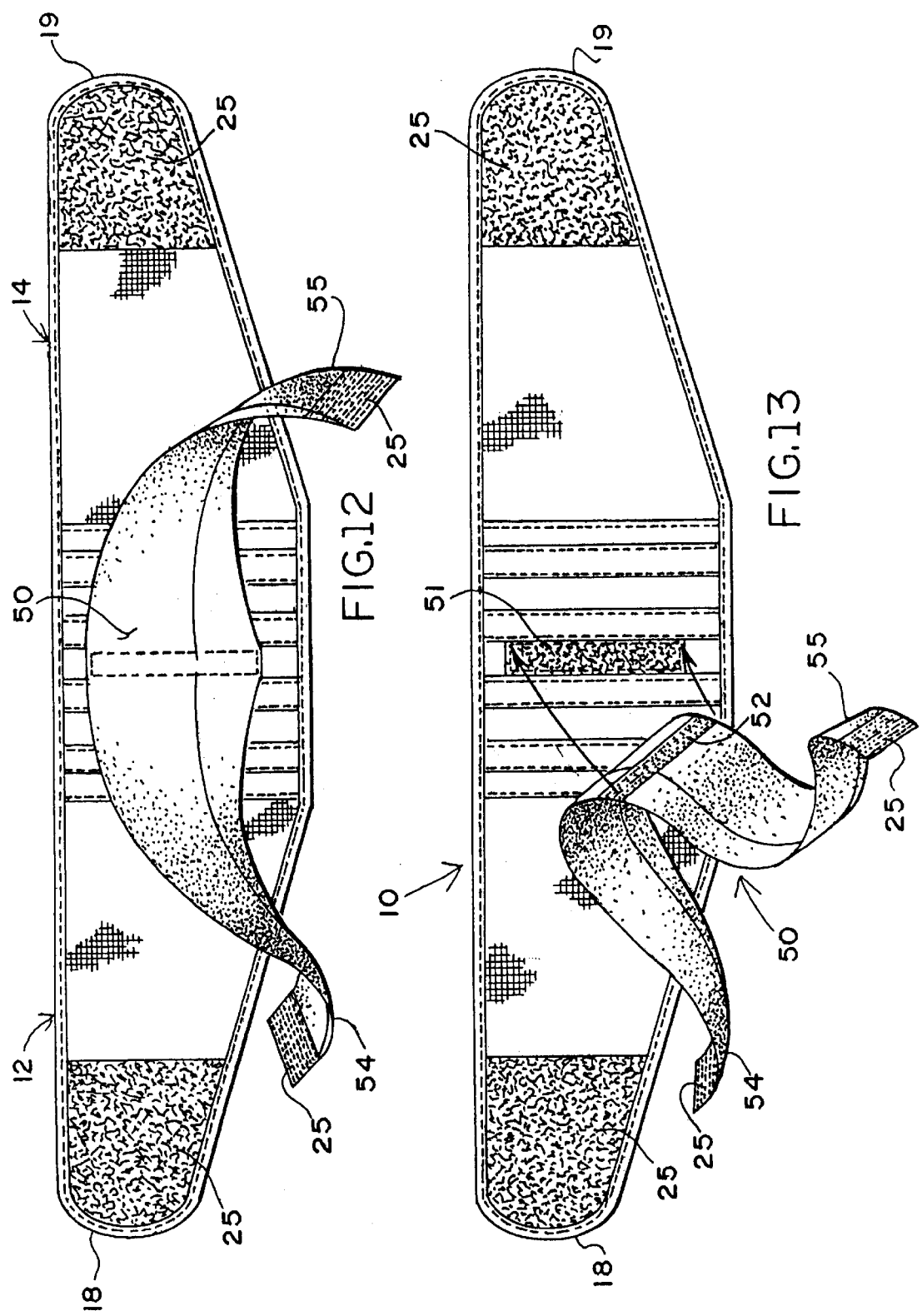

BACK BELT AND METHOD

FIELD OF THE INVENTION

The present invention is directed to back belts, and more particularly the varieties which are used in warehouses by people who are constantly lifting, nurses in hospitals and operating rooms, and delivery personnel. An important purpose of the belt is to assist in applying restraint to the users so that the back does not get into an awkward position prior to lifting and thus induce damage to the spine.

BACKGROUND OF THE INVENTION

Back belts abound in the prior art. Representative of such a back belt is Applicant's own U.S. Pat. No. 5,147,261, issued Sep. 15, 1992, relating to a lifting type belt. The subject belts when worn pursuant to a rigid safety program can significantly reduce the injuries in backs in various applications where lifting is involved irrespective of the weight. For example, in child care environments, quite often one of the attendants will lift a 15 to 20 pound child but, when the back is curved improperly, injury can result.

In addition, the standard back belts primarily employ wraps which extend laterally from a compression pad or back pad which is worn in the lumbar portion of the back. The wraps typically secure themselves one to the other with a releasable securable material well known by the Trademark VELCRO®. The back of the belt itself, and more particularly the compression pad, is somewhat complicated to manufacture and the positioning of the components, including stays and webbing which secures the stays in place, often times become misaligned. Moreover, the material employed can result in migrating upwardly or downwardly or rolling on the torso of the user. This can result in misorientation of the back belt, and stabilization of the spine, as should be done.

Furthermore, depending upon body shape and sizing, the stays may position themselves in a way to cause some discomfort to the users, and not perfectly positioned for optimum function. In use, the stays whether formed from plastic or steel, exert pressure against the threads of the stay pockets which are sewn in place. When such threads become worn, a workout or tearing of the threads can occur, rendering the back support less effective. Finally, but not all inclusively, the gripper material utilized for inside contact against the clothing of the wearer rubs off with time and wear and thus the grippers become ineffective. A concomitant problem arises from the fact that the surface area of the gripper material is generally insufficient to hold the back support in position without excessive movement.

SUMMARY OF THE INVENTION

The present invention stems from the new use of a formable plastic polyolefin material; one preferred embodiment being sold by the Trademark VOLARA®. The plastic foam is formable by a variety of techniques which are available. While the material is semi-rigid, it is sewable and commonly available with laminations to a variety of fabrics. Thus, the subject formable material can have one fabric laminated to one surface, and a different fabric laminated to the other surface.

In the method of the invention, which relates to the product of the invention, the formable material, with the fabric laminated preferably to both surfaces, is either cut to shape by standard clickers, heat cutting, or other means and then inserted into a die mold where it is formed by compression and heat. The compression and heat are primarily directed to forming channels for the stays to be later inserted, but also to form the lateral edge tongues and pockets for securement of the inner belt ends.

The VOLARA® material in the present invention is desirably laminated on both sides with the external laminate being a nylon, a mesh, sewable fabric. On the other hand, the inside laminate is a coated non-slip copolymer material.

Once the compression pad is formed to shape, the stays are placed in position in the stay channels and webbing applied over the stays and stitched to form a pocket for the stays along with the channel, and thereby secure the integrity of the back portion of the lift belt. The outer peripheral portion of the entire unit has a ribbing applied and the same, by way of binding effect, assists in securing the components together.

A supplementary embodiment of the invention relates to the utilization of a detachable back belt, which is the subject of Applicant's U.S. Pat. No. 5,656,021. It permit the advantages of supplementary belt usage when heavy loads are contemplated, and also has the advantage of being separately cleaned.

ADVANTAGE OF THE INVENTION

In view of the foregoing, it is a principle object of the present invention to provide a back belt with a new type back support compression pad member which is sufficiently integral due to the molding of the compression pad that uniformity in product will result in manufacture.

A related object is to form a back belt with a compression pad portion in which the stays are spaced from the back of the user, thereby eliminating undesirable pressure points and chaffing.

Yet another object of the present invention looks to the method of forming a back belt in which the inner wraps and outer wraps can be secured to the back belt portion, thereby eliminating a significant amount of wrap material.

Furthermore, it is an object of the present invention to form a thin back belt which enhances its appearance on the user of the belt.

DESCRIPTION OF ILLUSTRATIVE DRAWINGS

Further objects and advantages of the present invention will become apparent as the following description of an illustrative embodiment proceeds, taking in conjunction with the accompanying drawings in which:

FIG. 3 shows that the inner wraps on the right hand side are in flat orientation along with the outer wrap (not shown);

Figure 1:
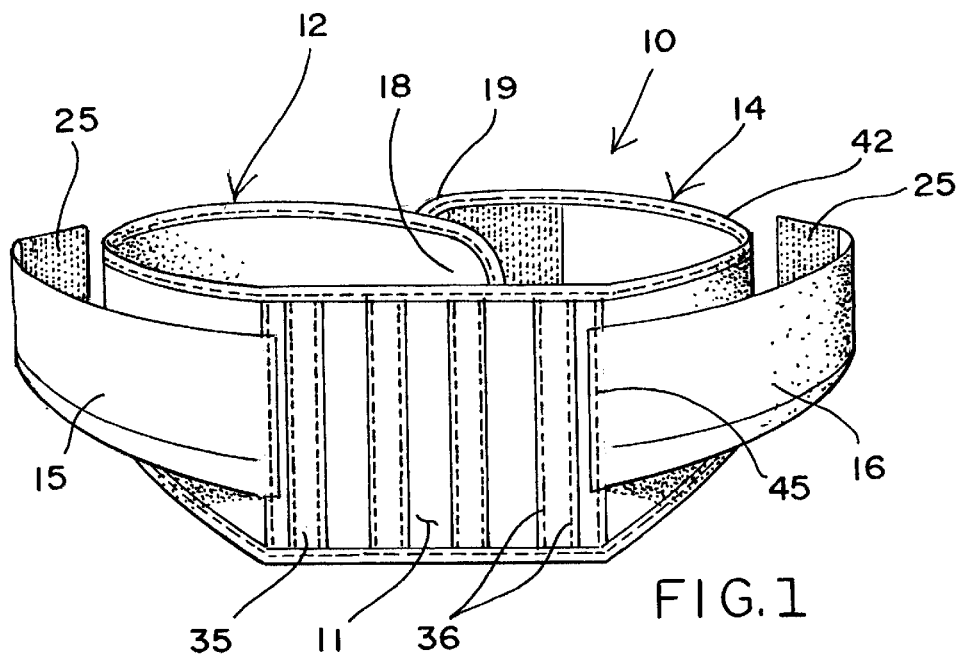
FIG. 1 is a perspective view of an illustrative back belt looking at the same from the back portion thereof. The inner wraps are overlapped, but the outer wraps are extended laterally from the back belt.

FIG. 4, in the sequence of securing the same to the torso, shows how the right hand inner wrap is secured around to the front portion of the abdomen of the user;

FIG. 5 shows diagrammatically by the arrows the action of placing into position the outer wraps, when the inner wraps have already been placed in overlapping and removable secured relationship each to the other;

FIG. 6 shows the entire back belt totally overlapped with the outer wraps secured to the inner wraps at the end portions of the outer wraps. It will be noted that the inner portion shows no chaffing elements to engage the torso of the user;

FIG. 7 is a broken, partially exploded, view of the compression pad prior to forming;

FIG. 8 is a view subsequent to that of FIG. 7 showing how the stays grooves are formed into the pad of FIG. 7, and also illustrating how the ends are prepared for receipt of the inner wraps and outer wraps for stitching into place.

FIG. 9 is yet a more detailed view of FIG. 8 showing the stay, stay web, inner wrap, and outer wrap positioned in place for stitching to the formed compression pad;

FIG. 10 is but a further sequential view showing how the stays are positioned into the stay grooves and then subsequently covered by the stay webbing, and also showing how the binding is secured around the periphery of the entire belt in order to assist in retaining the components, particularly the stays, in place;

FIG. 11 is a completed view of the outside of the belt ready for positioning on the person wearing the same;

FIG. 12 is a view of a supplementary embodiment of the back belt showing an auxiliary independent outer wrap; and FIG. 13 is a figure subsequent to FIG. 12 in the same scale and in exploded fashion showing how the detachable outer wrap is removed and replaced in use for operation.

DESCRIPTION OF PREFERRED EMBODIMENT

The preferred embodiment of the subject back support 10 appears in all figures of the drawings in one form or another. Beginning with FIG. 1, it will be seen that the back support 10 has a base or compression pad 11 provided at the center of the back, and intended to engage the lumbar portion of the user. The base 11 has secured at its lateral ends, the left inner wrap 12, and a right inner wrap 14. These are secured to each other at the left inner wrap end 18 and the right inner wrap end 19. The details will be set forth in conjunction with FIGS. 2 through 10 of the drawings and the description which follows later.

Figure 2:
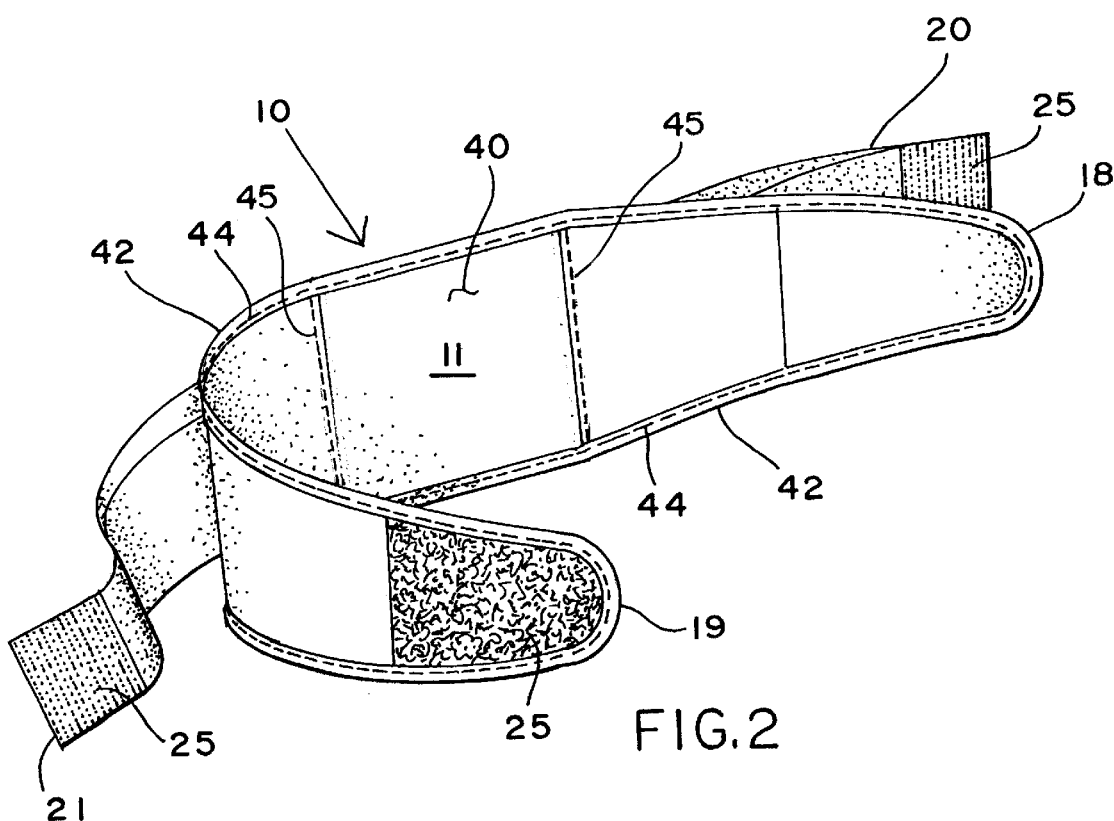
FIG. 2 is a perspective view of the same belt shown in FIG. 1, but taken from the inside, and without the inner wraps being secured over the others. The outer wraps are similarly free.

The end side of the belt 10 in partially perspective form while partially curved for engaging the body is shown in FIGS. 2, 3 and 4. There it will be seen that the base 11 presents a coated non-skid material 40 to the back portion of the user, as distinguished from the stays webbing 35 secured by means of stay webbing stitching to the back 11 as shown in FIG. 1. In addition, as shown in FIGS. 2 and 10 a binding 42 is secured around the entire peripheral edge of the inner wraps belt 10. The same is secured in place by binding stitch 44 (also shown in FIG. 10).

Turning now to FIG. 3, it will be seen that the left inner wrap 12 is at the right hand portion of the figure and shown in plan view. The left inner wrap end 18 has a removable securable material 25 secured and facing exteriorly of the left inner wrap end 18, as shown in FIG. 4. The right inner wrap 14 has a removable securable material 25 at its end, for overlapping engagement with the opposite end. As shown in FIG. 4, the left inner wrap 12 is being moved into place for overlapping engagement with the right inner wrap 14. Continuing now to FIG. 5, it will be seen that the left end 18 of inner wrap 12 has been overlapped by the right inner lap end 19 and the removable securable material 25 on the left wrap end 18 is underneath removable securable material underneath the right end of the right wrap (see FIG. 4). FIG. 5 shows, as stated, the inner wraps 12 and 14 secured to each other, and then diagrammatically indicates how the two outer wraps 15 and 16 are to be secured in overlapping relationship to the end portions of the inner wrap, as finally shown in FIG. 6.

FIG. 7 shows a portion of the base 11 but "dissected" for purposes of illustrating the building block material. The building block material includes the compression pad 30 which is sold by the name VOLARA®. The VOLARA® has laminated to it the coated non-slip material 40. Such material which may be used is a 50/50 poly/cotton circular knit fabric, with a coating of a proprietary PVC formulation sold under the name TOUGHTEK supplied by Harrison Technologies. The outer nylon material 41 is available in several varieties but it must be a nylon or equivalent sewable fabric, and susceptible of lamination to the pad 30. As to the pad 30. It Is a fine cell cross-linked polyolefin foam having a fine celled manufactures density of 12A. Closed cell cross-linked polyethylene foam or closed celled polyurethane foam are also available, if they meet the criteria of being sewable, and formable. Such materials are manufactured by the VOLTEK Division of SEKISUI American Corporation, and are laminated by UPF Technologies.

The stays 31 may be plastic or metal. Particularly with reference to FIGS. 9 and 10, it will be seen that the stay 31 is formed to fit within the stay groove 32 which, with the stay web 35, stitched in place by the stay stitches 36, forms a stay pocket 34. When the binding 42 is stitched in place, particularly as diagrammatically shown in FIG. 10 by means of binding stitching 44. The stays 31 are locked in the stay pocket 34 and therefore will not migrate upwardly or downwardly. Further in accordance with the invention, the groove 32, as shown previously in FIG. 8, is formed primarily by means of heat compression molding of the compression pad VOLARA® material 30. This is done on a flat platen with male heated members or male platen compressing the foam 30 to the point where the stay grooves 32 (again as shown in FIG. 8), comprise approximately half of the depth of the compression pad material 30. Thereafter, and also as shown somewhat diagrammatically in FIGS. 9 and 10, the webbing 35 is applied over the stays 31, and secured in place by the stay stitches 36 in the webbing 35.

The details of completing the securement of the inner wrap and outer wrap may best be appreciated from a review of FIGS. 8, 9 and 10. Beginning with FIG. 8, it will be seen that the compression pad 30, with its outer coat and its inner coat, is formed to form stay grooves 32. The stays 31 are slipped into the stay grooves, particularly as shown in FIG. 9. Thereafter, the stay web 35 is applied over the stays 31, and the same are secured in place by stay stitches 36. When the back portion is completed, particularly as shown in FIGS. 9 and 10, it will be seen that the coated non-slip inner material 40 is the material that goes against the clothing of the person wearing the back belt. The wrap and the outer mesh are as shown. As shown in considerable detail in FIGS. 8 and 9, there is a inner wrap recess 38 provided at the lateral edges of the compression pad 30, and an outer wrap recess 39 opposed to the inner wrap recess. The purpose is as shown in FIG. 9, namely, to receive the ends of the inner wrap 14 and the outer wrap 16, so that when the same are stitched in place they will continue to contribute to the slim profile presented by the completed compression pad 30. Finally, the entire structure is secured together, particularly as shown in FIG. 10, by running a binding 42 around the entire peripheral edge of the back belt, including the inner wrap, and the same is secured in place by binding stitch 44. Wrap stitch 45, as shown in FIGS. 9 and 10, secure the wraps in place.

A further alternative embodiment is shown in FIGS. 12 and 13 where it will be seen that the detachable outer wrap 50 is removably secured to the compression pad 30. It is secured by means of removable securable members 51, 52 matingly engaging between the detachable outer wrap 50 and the compression pad portion of the belt 10. The ends 54, 55 of the outer wrap 50 are secured to the ends 25 of the main belt. This embodiment omits the outer wrap 15, 16 of the main embodiment. The subject matter of the removable securable belt is shown and described in Applicant's U.S. Pat. No. 5,656,021, issued Aug. 12, 1997. However, in that case it is not employed in conjunction with the advantageous compression pad of the present invention.

METHOD OF THE INVENTION

The present invention is directed to the method of forming, as illustrated, a base 11 for a back support 10 in which a back support 30 is utilized as the main portion of the back 11. The steps involved of cutting or clipping the blank to the form are essentially shown in FIGS. 7 and 8. However prior thereto, the coated non-slip inner laminated material 40 and woven mesh material 41 are laminated to the compression pad 30.

After the stay grooves 32 have been formed, as described above, the stays 31 are then positioned into the groove 32. the webbing 35 applied as shown in FIG. 9 and then the webbing stitched in place with web stitching 36. The compression pad ends of the inner wrap 14 and outer wrap 10 are positioned in place in the inner wrap recess 38 and outer wrap recess 39. as shown in FIG. 9. Thereafter they are stitched in place in the same general fashion as the webbing 35 over the stays 31. Finally, as shown in FIG. 10, the binding 42 is stitched in place by means of wrap stitching 44. It is to be emphasized again that the binding 42 is positioned in place after the stay web 35 are stitched in place by means of the stay stitches 38. and the inner portions of the inner wrap 14 and the outer wrap 16 are stitched in place by means of wrap stitches 45. The binding 42 and its stitching 44 thus provide a means for closing the ends of the stay pockets 34.

It will be understood that various changes in the details, materials and arrangements of parts, or method which have been herein described and illustrated in order to explain the nature of the invention, may be made by those skilled in the art within the principle and scope of the invention as expressed in the appended claims.

What is claimed is:

1. A back belt comprising in combination;
a compression pad having inner and outer faces and upper and lower edges extending between lateral ends and being proportioned for overlapping the lumbar area of the back of users;
said compression pad being an integrally formed composite of a cellular foam heat formable material laminated between a copolymer coated non-slip fabric material laminate forming said inner face and a mesh fabric material laminate forming said outer face of said compression pad, all of said laminated materials being stitchable and formable;
a plurality of spaced narrow substantially parallel stay grooves die molded into said outer face fabric material and the foam material laminated thereto, said grooves extending between said upper and lower edges of said compression pad;
a plurality of stays inserted into and being wholly received within said grooves formed into said compression pad;
webbing secured over the stays once in place within said grooves to define a plurality of stay pockets;
a first pair of wraps separate from said compression pad extending from said compression pad for wrapping around the torso of the body of users and having inner ends fastened to said lateral ends of said compression pad and extending outwardly therefrom to distal wrap ends;
a second pair of wraps separate from said compression pad extending from said compression pad for wrapping around said first pair of wraps, said second pair of wraps having inner ends fastened to said lateral ends of said compression pad and extending outwardly therefrom to distal wrap ends;
said inner ends of said first and second pairs of wraps being secured to said lateral ends of said compression pad by stitching to and through said inner ends of said first and second pairs of wraps, said foam material, said inner non-slip material, and said outer fabric material laminated to said foam material;
first recesses formed into said lateral ends of said compression pad, said first recesses extending into said non-slip inner face material and into said foam material laminated thereto, said first recesses receiving said inner ends of said first pair of wraps;
second recesses formed into said lateral ends of said compression pad, said second recesses extending into said fabric outer face material and into said foam material laminated thereto, said second recesses receiving said inner ends of said second pair of wraps,
said inner ends of said first and second pair of wraps being secured in said recesses by said stitching through said wrap ends and through all laminates of said lateral ends of said composite compression pad;
said upper and lower edges of said compression pad and the periphery of said first pair of wraps being covered by a peripheral binding extending therearound and secured thereto by stitching through said peripheral binding and said laminated fabric and foam materials of said composite compression pad and the periphery of said first pair of wraps,
said securement of said peripheral binding to said composite compression pad closing said stay grooves holding said stays longitudinally in place in said grooves by means of said peripheral covering sewn to and through said foam and said laminated inner and outer faces.

* * * * *